United States Patent
Soon-Shiong et al.

(10) Patent No.: US 11,050,720 B2
(45) Date of Patent: *Jun. 29, 2021

(54) HOMOMORPHIC ENCRYPTION IN A DATA PROCESSING NETWORK ENVIRONMENT, SYSTEM AND METHODS

(71) Applicant: NANTHEALTH, INC., Culver City, CA (US)

(72) Inventors: Patrick Soon-Shiong, Culver City, CA (US); Harsh Kupwade-Patil, Plano, TX (US); Ravi Seshadri, Plano, TX (US); Nicholas J. Witchey, Laguna Hills, CA (US)

(73) Assignee: NANTHEALTH, INC., Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/939,360

(22) Filed: Jul. 27, 2020

(65) Prior Publication Data

US 2020/0358746 A1 Nov. 12, 2020

Related U.S. Application Data

(63) Continuation of application No. 16/679,078, filed on Nov. 8, 2019, now Pat. No. 10,757,081, which is a
(Continued)

(51) Int. Cl.
*H04L 29/06* (2006.01)
*H04L 9/00* (2006.01)
(Continued)

(52) U.S. Cl.
CPC ...... *H04L 63/0428* (2013.01); *G06F 21/6245* (2013.01); *G16H 40/20* (2018.01);
(Continued)

(58) Field of Classification Search
None
See application file for complete search history.

(56) References Cited

U.S. PATENT DOCUMENTS 8,260,845 B1 * 9/2012 Colton .................. G06F 8/30
709/203
8,271,796 B2 9/2012 Diamond
(Continued)

FOREIGN PATENT DOCUMENTS

| EP | 2709028 | 3/2014 |
|---|---|---|
| JP | 2013150026 | 8/2013 |

(Continued)

OTHER PUBLICATIONS

Briscoe et al., "Digital Ecosystems in the Clouds: Towards Community Cloud Computing", 3rd IEEE International Conference on Digital Ecosystems and Technologies, 2009 (Year: 2009).*
(Continued)

*Primary Examiner* — Henry Tsang
(74) *Attorney, Agent, or Firm* — Stetina Brunda Garred and Brucker

(57) ABSTRACT

A system and method for homomorphic encryption in a healthcare network environment is provided and includes receiving digital data over the healthcare network at a data custodian server in a plurality of formats from various data sources, encrypting the data according to a homomorphic encryption scheme, receiving a query at the data custodian server from a data consumer device concerning a portion of the encrypted data, initiating a secure homomorphic work session between the data custodian server and the data consumer device, generating a homomorphic work space associated with the homomorphic work session, compiling, by the data custodian server, a results set satisfying the query, loading the results set into the homomorphic work space, and building an application programming interface
(Continued)

(API) compatible with the results set, the API facilitating encrypted analysis on the results set in the homomorphic work space.

21 Claims, 4 Drawing Sheets

Related U.S. Application Data continuation of application No. 16/228,572, filed on Dec. 20, 2018, now Pat. No. 10,476,853, which is a continuation of application No. 15/727,494, filed on Oct. 6, 2017, now Pat. No. 10,200,347, which is a continuation of application No. 14/805,417, filed on Jul. 21, 2015, now Pat. No. 9,819,650.

(60) Provisional application No. 62/027,643, filed on Jul. 22, 2014.

(51) Int. Cl.
*G16H 40/20* (2018.01)
*G06F 21/62* (2013.01)
*H04L 9/32* (2006.01)
*G16Z 99/00* (2019.01)

(52) U.S. Cl.
CPC .............. *G16Z 99/00* (2019.02); *H04L 9/008* (2013.01); *H04L 9/32* (2013.01); *H04L 9/3218* (2013.01); *H04L 63/0442* (2013.01); *H04L 63/08* (2013.01); *H04L 2209/88* (2013.01)

(56) References Cited

U.S. PATENT DOCUMENTS

| | | | |
|---|---|---|---|
| 8,316,237 B1 | 11/2012 | Felsher et al. | |
| 8,555,400 B2 | 10/2013 | Shi et al. | |
| 8,565,435 B2 | 10/2013 | Gentry et al. | |
| 8,627,107 B1 | 1/2014 | Kennedy et al. | |
| 8,630,422 B2 | 1/2014 | Gentry | |
| 8,880,867 B2 | 11/2014 | Jawurek et al. | |
| 9,077,525 B2 | 7/2015 | Chandran et al. | |
| 9,083,526 B2 * | 7/2015 | Gentry | H04L 9/3093 |
| 9,118,631 B1 | 8/2015 | Yung et al. | |
| 9,252,942 B2 | 2/2016 | Zhang et al. | |
| 9,276,911 B2 | 3/2016 | Wang et al. | |
| 9,449,191 B2 | 9/2016 | MacCarthy et al. | |
| 2005/0108709 A1 * | 5/2005 | Sciandra | G06F 9/505 |
| | | | 718/1 |
| 2006/0123028 A1 * | 6/2006 | Timothy Fong | G06F 11/362 |
| 2006/0245587 A1 | 11/2006 | Pinkas et al. | |
| 2007/0143823 A1 * | 6/2007 | Olsen | G06F 21/6218 |
| | | | 726/1 |
| 2008/0133699 A1 * | 6/2008 | Craw | G16H 40/20 |
| | | | 709/217 |
| 2009/0216558 A1 | 8/2009 | Reisman et al. | |
| 2009/0307486 A1 * | 12/2009 | Grajek | H04L 63/123 |
| | | | 713/156 |
| 2009/0313463 A1 | 12/2009 | Pang et al. | |
| 2011/0110525 A1 | 5/2011 | Gentry et al. | |
| 2012/0331283 A1 | 12/2012 | Chandran et al. | |
| 2013/0086390 A1 * | 4/2013 | Kennedy | G06F 21/62 |
| | | | 713/189 |
| 2013/0097417 A1 | 4/2013 | Lauter et al. | |
| 2013/0275743 A1 | 10/2013 | Jawurek et al. | |
| 2013/0275752 A1 | 10/2013 | Zhang et al. | |
| 2014/0075183 A1 | 3/2014 | Wang et al. | |
| 2014/0121990 A1 | 5/2014 | Baldi et al. | |
| 2014/0140514 A1 | 5/2014 | Gentry | |
| 2014/0177828 A1 * | 6/2014 | Loftus | H04L 9/0852 |
| | | | 380/44 |
| 2014/0195269 A1 | 7/2014 | Sircar et al. | |
| 2014/0281511 A1 | 9/2014 | Kaushik et al. | |
| 2014/0289536 A1 | 9/2014 | MacCarthy et al. | |
| 2015/0154357 A1 | 6/2015 | Biswas et al. | |
| 2015/0154406 A1 * | 6/2015 | Naehrig | G06F 21/602 |
| | | | 713/165 |
| 2015/0304329 A1 | 10/2015 | Yan et al. | |
| 2015/0365431 A1 * | 12/2015 | Iliev | G06F 21/62 |
| | | | 726/23 |
| 2018/0165780 A1 | 6/2018 | Romeo | |

FOREIGN PATENT DOCUMENTS

| | | |
|---|---|---|
| WO | 2014011633 | 1/2014 |
| WO | 2014040964 | 3/2014 |
| WO | 2014057369 | 4/2014 |

OTHER PUBLICATIONS

Cousins et al., "SIPHER: Scalable Implementation of Primitives for Homomorphic EncRyption—FPGA implementation using Simulink", Sep. 2011 (Year: 2011).*
Patil, Harsh Kupwade; Seshadri, Ravi; "Big Data Security and Privacy Issues in Healthcare", 2014 IEEE International Congress on Big Data, Dallas, US, 2014.
Gentry, Craig; Groth, Jens; Ishai, Yuval; Peikert, Chris; Sahai, Amit; Smith, Adam; "Using Fully Homomorphic Hybrid Encryption to Minimize Non-Interactive Zero-Knowledge Proofs", Journal of Cryptology, pp. 1-22, Apr. 18, 2014 2014.
Damgard, Ivan; Pastro, Valerio; Smart, Nigel; Zakarias, Sarah; "Multiparty Computation from Somewhat Homomorphic Encryption", Department of Computer Science, Aarhus University; Department of Computer Science, Bristol University; International Association for Cryptologic Research 2012, CRYPTO 2012, LNCS 7417, pp. 643-662, 2012.
Smart, Nigel P.; Vercauteren, Frederik; "Fully Homomorphic Encryption with Relatively Small Key Ciphertext Sizes", Dept. Computer Science, University of Bristol, Bristol, UK; COSIC—Electrical Engineering, Katholieke Universiteit Leuven, Heverlee, Belgium; International Association for Cryptologic Research 2010, PKC 2010, LNCS 6056, pp. 420-443, 2010.
Gentry, Craig; Halevi, Shai; "Implementing Gentry's Fully-Homomorphic Encryption Scheme", IBM Research, International Association for Cryptologic Research 2011, Eurocrypt 2011, LNCS 6632, pp. 129-148, 2011.
Fontaine, Caroline; Garland, Fabien; "A Survey of Homomorphic Encryption for Nonspecialists", Hindawi Publishing Corporation, EURASIP Journal on Information Security, vol. 2007, Article ID 13801, 10 pages, doi:10.1155/2007/13801.
Gentry, Craig; "Fully Homomorphic Encryption Using Ideal Lattices", presented at the Proceedings of the forty-first annual ACM symposium on Theory of computing, Bethesda, MD, USA, pp. 169-178, 2009.
Brickell, Ernest F.; Yacobi, Yacov; "On Privacy Homomorphisms (extended abstract)", Bell Communications Research, Morristown, New Jersey; Springer-Verlag Berlin Heidelberg 1988, Advances in Cryptology—EUROCRYPT 87, LNCS 304, pp. 117-125, 1988.
Rivest, Ronald L.; Adleman, Len; Dertouzos, Michael L.; "On Data Banks and Privacy Homomorphisms", Massachusetts Institute of Technology, Cambridge, MA, Academic Press, Inc., 1978.
Tucker, Patrick; "Has Big Data Made Anonymity Impossible?", pp. 2-4, MIT Technology Review 2013.
Volkhausen, Tobias; "Paillier Cryptosystem: A Mathematical Introduction", pp. 1-10, Mar. 10, 2006.
Zyskind, Guy; Nathan, Oz; Pentland, Alex 'Sandy'; "Enigma: Decentralized Computation Platform with Guaranteed Privacy", pp. 1-14. Jun. 10, 2015.
"Paillier's Cryptosystem" Chapter 3, pp. 29-59. http://www.ippari.unict.it/~catalano/Corsi/Tesi-Cap3-Paillier.pdf. downloaded Jun. 3, 2014 (estimated).
Gentry, Craig; "A Fully Homomorphic Encryption Scheme—A Dissertation Submitted to the Department of Computer Science and the Committee on Graduate Studies of Stanford University in Partial Fulfillment of the Requirements for the Degree of Doctor of Philosophy", pp. 1-209, Craig Gentry Sep. 2009.

(56) References Cited

OTHER PUBLICATIONS

Halevi, Shai; Shoup, Victor; "Algorithms in HElib", IBM Research, pp. 1-18, Intelligence Advanced Research Projects Activity (IARPA) via Department of Interior National Business Center (DoI/NBC) contract No. D11PC20202, 2014.

Brakerski, Zvika; Gentry, Craig; Vaikuntanathan, Vinod; "Fully Homomorphic Encryption without Bootstrapping", presented at the Proceedings of the 3rd Innovations in Theoretical Computer Science Conference, Cambridge, Massachusetts, 2012.

Yao, Andrew Chi-Chih; "How to Generate and Exchange Secrets (extended abstract)",Department of Computer Science, Princenton University, Princeton, NJ, IEEE,1986.

"Mikeivanov/paillier •GitHub—Pure Python Paillier Homomorphic Cryptosystem", https://github.com/mikeivanov/paillier. Aug. 7, 2011 (estimated).

Dubuisson, Thomas M.; "Secure Computation with HELib—The Type-Safe Jabberwolk", pp. 1-6, Posted May 13, 2013. http://tommd.github.io/.

"Quantum key distribution technology: Secure computing for the 'Everyman'." Phys.org. Sep. 3, 2014.

"Shaih/HElib—GitHub—An Implementation of homomorphic encryption", https://github.com/shaih/HElib, Mar. 31, 2013 (estimated).

Zhumatov, Amir; Tulepbergenov, Yelnar; "Paillier cryptosystem (presentation)", Slides 1-21. Uploaded Date Sep. 9, 2014. Date Unknown.

Authorized Officer Kim, Do Weon, "International Search Report" dated May 9, 2016. PCT/US2015/041635. 3 pages.

Authorized Officer Kim, Do Weon, "The Written Opinion of the International Searching Authority" dated May 9, 2016. PCT/US2015/041635. 5 pages.

\* cited by examiner

HOMOMORPHIC ENCRYPTION IN A DATA PROCESSING NETWORK ENVIRONMENT, SYSTEM AND METHODS

CROSS-REFERENCE TO RELATED APPLICATION

This application is a continuation of U.S. application Ser. No. 16/679,078, filed Nov. 8, 2019, which is a continuation of U.S. application Ser. No. 16/228,572, filed Dec. 20, 2018, now U.S. Pat. No. 10,476,853 issued Nov. 12, 2019, which is a continuation of U.S. application Ser. No. 15/727,494, filed Oct. 6, 2017, now U.S. Pat. No. 10,200,347 issued Feb. 5, 2019, which is a continuation of U.S. application Ser. No. 14/805,417, filed Jul. 21, 2015, now U.S. Pat. No. 9,819,650 issued Nov. 14, 2017, which claims the benefit of priority under 35 U.S.C. § 119(e) to U.S. Provisional Patent Application Ser. No. 62/027,643, filed on Jul. 22, 2014 and entitled SYSTEM AND METHOD FOR HOMOMORPHIC ENCRYPTION IN A HEALTHCARE NETWORK ENVIRONMENT, the disclosures of which are hereby incorporated by reference in their entirety.

TECHNICAL FIELD

This disclosure relates in general to the field of healthcare systems and, more particularly, to systems and methods related to homomorphic encryption in a healthcare network environment.

BACKGROUND

The background description includes information that may be useful in understanding the present disclosure. It is not an admission that any of the information provided herein is prior art or relevant to the disclosure, or that any publication specifically or implicitly referenced is prior art.

The healthcare industry is going through a digital revolution stimulated in part by the American Recovery and Reinvestment Act of 2009. Modernizing healthcare has led to a new age of digital health and wellness, in which healthcare data is collected from disparate sources (e.g., sensors connected to patients), and stored in disparate healthcare clouds (e.g., private, community and public clouds). Moreover, the volume of agglomerated healthcare data is large enough to qualify as "big data". As healthcare clouds become a prominent feature in the healthcare industry, there is a greater need for securely sharing patient information across such disparate healthcare clouds. Furthermore, with Accountable Care Organizations (ACOS) (e.g., healthcare care providers such as doctors, hospitals and insurance providers) coming together to provide high-quality care in a cost-effective manner, demand for seamless connectivity across the healthcare clouds is greater than ever. A simplified patient-centric model is desirable where patients can change providers and still share their information in a timely manner, for better diagnosis and treatment, and eventually for improved global health.

At present, healthcare providers who host sensitive patient data in private healthcare clouds across the globe are hesitant to share that information because of security and privacy issues. As healthcare providers move to community and public cloud based services, a need for secure interaction between disparate healthcare clouds increases. Furthermore, security regulations imposed by Health Insurance Portability and Accountability Act (HIPAA) and Health Information Technology for Economic and Clinical Health (HITECH) place an onerous task on healthcare Information Technology (IT) infrastructure to be compliant with privacy and security regulations. In addition, with emerging Internet of Things (IoT) market and its integration in the big data cloud platform, there is increased concern about security and privacy with the healthcare cloud paradigm.

SUMMARY

Apparatus, systems and methods for homomorphic encryption in a healthcare network environment is provided and includes receiving data at a data custodian server in a plurality of formats from various data sources, encrypting the data according to a homomorphic encryption scheme, receiving a query at the data custodian server from a data consumer device concerning a portion of the encrypted data, initiating a secure homomorphic work session between the data custodian server and the data consumer device, generating a homomorphic work space associated with the homomorphic work session, compiling, by the data custodian server, a results set satisfying the query, loading the results set into the homomorphic work space, and building an application programming interface (API) compatible with the results set, the API facilitating encrypted analysis on the results set in the homomorphic work space.

Various objects, features, aspects and advantages of the subject matter will become more apparent from the following detailed description of preferred embodiments, along with the accompanying drawing figures in which like numerals represent like components.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DETAILED DESCRIPTION OF EXAMPLE EMBODIMENTS

Example Embodiments

Figure 1:
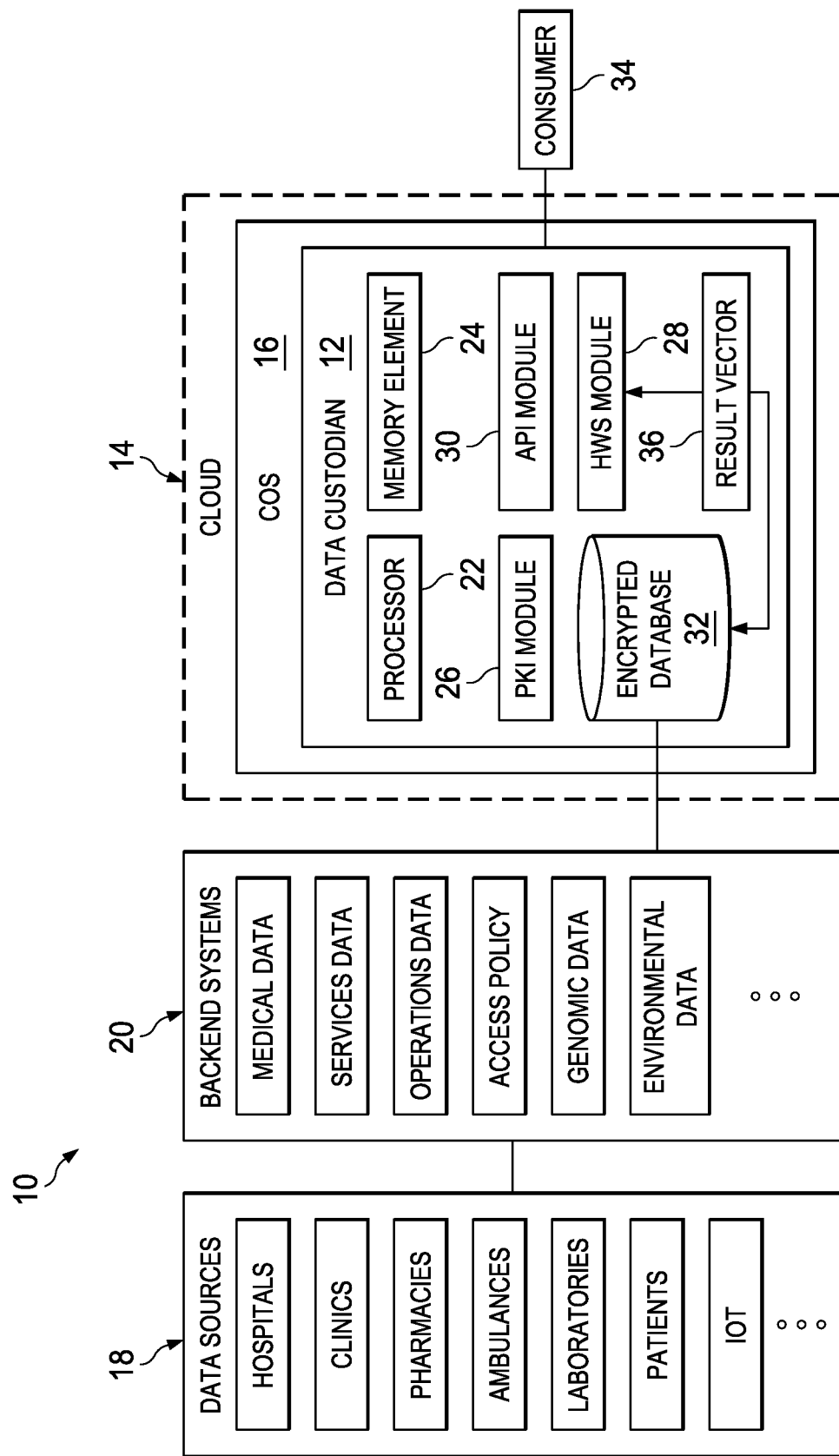
FIG. 1 is a simplified block diagram illustrating a system facilitating homomorphic encryption in a healthcare network environment according to an example embodiment.

Turning to FIG. 1, FIG. 1 is a simplified block diagram illustrating a system 10 according to an example embodiment. System 10 includes a data custodian 12 executing in a cloud 14 that may be configured with a clinical operating system (cOS) 16. As used herein, the term "cloud" includes a collection of hardware and software forming a shared pool of configurable computing resources (e.g., networks, servers, storage, applications, services, etc.) that can be suitably provisioned to provide on-demand self-service, network access, resource pooling, elasticity and measured service, among other features. Cloud 14 may be deployed as a private cloud (e.g., infrastructure operated by a single enterprise/organization), community cloud (e.g., infrastructure shared by several organizations to support a specific community that has shared concerns), public cloud (e.g., infrastructure made available to the general public), or a suitable combination of two or more disparate types of clouds. Cloud 14 may be managed by a cloud service provider, who can provide subscribers with access to the cloud and authorization to use cloud resources in accordance with predetermined service level agreements.

Various data sources 18 (e.g., hospitals, clinics, pharmacies, ambulances, laboratories, patients, medical devices comprising an Internet of Things (IOT), etc.) may provide healthcare data to backend systems 20. The healthcare data may include blood pressure or heart monitor or blood sugar readings, for example, along with information about patients such as age, weight, gender, or other risk factors. The healthcare data may also include financial data (e.g., payments, cost of operations, etc.), and various other types of data. Virtually any type of data may be included within the broad scope of embodiments of system 10.

Backend systems 20 may analyze the healthcare data from data sources 18 and tag the data as (or extract therefrom) medical data, services data, operations data, access policies, genomic data, environmental data, social data, financial data, etc. In a general sense, backend systems 20 may characterize (e.g., categorize, tag, extract, describe, stamp, label, etc.) the healthcare data from data sources 18 in any suitable manner according to particular needs. The tagged data may be stored in an encrypted format with data custodian 12 in cloud 14.

In various embodiments, data custodian 12 may include one or more of a processor 22, a memory element 24, a public key infrastructure (PKI) module 26, a homomorphic work space (HWS) module 28, an application programming interface (API) module 30 and an encrypted database 32. Encrypted database 32 may store tagged data from data sources 18 in an encrypted format. In some embodiments, encrypted database 32 may be located in a single physical storage system (e.g., storage area network (SAN), network attached storage (NAS), redundant array of independent disks (RAID), etc.). In other embodiments, encrypted database 32 may comprise a distributed storage system, for example, storing its contents across various physical storage devices in a storage area network. In various embodiments, encrypted database 32 may be managed suitably, according to access control policies that limit access to its contents in a preconfigured manner.

In various embodiments, data custodian 12 may receive queries and other requests for data and/or data analysis from a consumer 34 concerning healthcare data from data sources 18, and may perform homomorphic encryption on the data and/or data analysis to generate a results vector 36, which may be returned to consumer 34 appropriately. According to various embodiments, HE-data can be stored in cloud 14 (e.g., in encrypted database 32), and consumer 34 can perform computations on the HE-data, without prior decryption.

As used herein, the term "consumer" is meant to encompass a computing device (e.g., computer, mobile device such as a smartphone or tablet, etc.) that includes a software application executing thereon that receives a digital data set (e.g., collection of data), and uses the data for further processing, such as queries, analysis, and reporting (among other purposes). Note that the consumer does not necessarily generate new data, but merely uses (e.g., processes, consumes, etc.) existing data. In some embodiments, consumer 34 refers to a destination for data from data custodian 12. Consumer 34 may be operated by an individual, entity (e.g., corporation), group, organization, etc. For example, consumer 34 may be operated by a cloud provider, analytics companies, or data owners. In some embodiments, consumer 34 may comprise a remote client that sends a query for certain healthcare data to data custodian 12.

For purposes of illustrating the techniques of system 10, the following foundational information may be viewed as a basis from which the present disclosure may be properly explained. Such information is offered earnestly for purposes of explanation only and, accordingly, should not be construed in any way to limit the broad scope of the present disclosure and its potential applications.

A study by International Data Corporation (IDC) shows that digital data, including healthcare data is doubling every two years worldwide. It was approximated at 2.8 zettabyte in 2012 and is predicted to double by 2015. In contrast, only 0.5 percent of the data is ever analyzed. Moreover, with the increasing popularity of Internet of Things (IoT), three-fourths of the data is likely to be consumer driven and will include personal data. As personal data related to healthcare (e.g., Personally Identifiable Information (PII), Protected Health Information (PHI), etc.) grows exponentially in the coming decade, individual consumer-patients may want to have full control of their personal data.

With introduction of the "Right to Know Act of 2013", initiated by the California legislative, data hosting entities would be mandated to disclose "personal information" to the concerned party (e.g., patient in the healthcare domain), which includes exposing their storage location and relevant IP addresses. In the context of healthcare, due to privacy and security concerns, patients should be the sole owners of their respective data and be able to exercise absolute control on their PHI. Consequently, there is a need for data custodians that can host the data, especially in secure fashion that respects privacy.

Nevertheless, storing data with data custodians without encryption could mean a complete loss of privacy. For example, in currently existing healthcare practices, a provider can be a custodian for patient data and can have complete access to all PHI. Because healthcare clouds are typically more susceptible to an insider attack (than from external sources), the responsibilities of providing security and privacy is placed on the provider. With medical data being extremely valuable, leakage of the consumer-patient's private health information can lead to bioterrorism. A conventional solution to resolving security and privacy concerns is to encrypt data using an asymmetric key cryptographic scheme wherein the end user (e.g., the patient) has sole access to the private key.

However, a limitation to this approach is that neither the custodian nor any third-party company can perform analytics prior to decrypting the data. Analyzing medical information, for example, for predictive analysis can be useful towards improving global health. However, there is an inherent risk associated with patient's privacy and security if advanced predictive analytics is performed on healthcare data (e.g., computations performed on PHI). Thus, although the conventional asymmetric key cryptographic scheme can be useful for security, performing mathematical operations on encrypted data without decrypting has been a long-standing problem in cryptography. Moreover, performing data analytics requires "informed consent" from the patient whose data is hosted by the provider and requires the provider to explain the risks and benefits of executing predictive models on the patient's data.

Turning to IoT in healthcare, the amount of data generated by medical devices such as wearable medical sensors (e.g., Fitbit® activity tracker, pulse oximeters, etc.) is enormous. Care providers may want to leverage machine-driven intelligent data analysis in a centralized or ad-hoc manner. However, like any wireless device, wireless IoT devices are accessible by devices operating in the same wireless frequency band and therefore are susceptible to attack. Furthermore, IoT devices can be more vulnerable because of their limited storage, computing and communication capabilities. For example, an IoT device transmitting vitals can be hacked easily since it does not have encryption at rest or in motion.

An approach to solving the data security problem is through a homomorphic encryption (HE) scheme that allows processing encrypted data that would produce results analogous to processing unencrypted data and obtain identical outcomes when decrypted. For example, results obtained by an arithmetic operation performed on plain text is identical to operations performed on ciphered text. HE represents a type of encryption technology that allows a computing device to operate on encrypted data without requiring the data to be decrypted. For example, consider a case where a computing device is commanded to conduct an addition operation on two numbers a and b. Ordinarily, the result would be calculated as follows: c=a+b. However, there can be circumstances under which it is desirable to restrict the computing device from accessing the values of a and b, while also retaining the capability of to add the numbers together. Assume that operator E( ) encrypts a value and D( ) decrypts a value according to a key and/or an implementation of a cryptographic algorithm. Thus, D(E(a))=a. It would be desirable to have an addition operator, e.g., ADD( ) such that: E(c)=ADD(E(a), E(b)), where D(E(c))=c=a+b.

Simple mathematical formulae can offer such simple properties; for example, exp(x), where E(x)=exp(x) and D(x)=ln(x). The ADD( ) operate would be an arithmetic multiplication. For example:
E(c)=ADD(E(a), E(b));
E(c)=ADD(exp(a), exp(b));
E(c)=exp(a)*exp(b);
E(c)=exp(a+b);
D(E(c))=ln(exp(a+b));
ln(exp(c))=ln(exp(a+b));
c=a+b.
However, the above approach may be too simplistic to be secure, for example, as it would be easy to decipher such encryption.

The problem of computing any function on encrypted data has been long recognized and stems back to work done by cryptographers Rivest, Adleman and Dertouzous on general privacy homomorphism, with homomorphic encryption as a subset. However, the schemes proposed then were proved to be not secure and the construction of a fully homomorphic encryption (FHE) scheme that facilitates unlimited additions and multiplications on cipher text has remained an open research problem for almost three decades.

In 2009, Craig Gentry constructed an FHE scheme based on ideal lattices, which has led to a new generation of cryptographic algorithms. Prior to Gentry's scheme, several homomorphic encryption schemes were proposed, but such schemes were only able to process encrypted data using either addition or multiplication operation. In addition, generating application-specific protocols required linearizing computations and involved multiparty computations. In Gentry's breakthrough scheme, any third party was able to perform complex computations on encrypted data using both addition and multiplication operations without knowing the decryption key. Furthermore, Gentry's scheme allows direct computation of permitted polynomial functions on encrypted data and eliminates the need for linearizing computations.

Gentry's blueprint includes a somewhat homomorphic encryption (SWHE) scheme and a bootstrapping mechanism. The SWHE, restricted to "low-degree" polynomial functions, permits unlimited additions and a bounded number of multiplication operations. In spite of the limitation, SWHE can process several functions used in various applications. To support a low-degree polynomial, the SWHE scheme squashes the decryption scheme. However, each arithmetic operation comes at a price. Computations on cipher texts are "noisy" and the noise increases exponentially with increase in multiplication operations. In the case of the bootstrapping mechanism, a SWHE scheme can evaluate its own decryption function using a secret key shared via a secure channel, resulting in reduced noise.

However, Gentry's scheme has several drawbacks including computational complexity and larger key sizes, thereby making them unusable in real applications. As a result, homomorphic encryption has not seen greater acceptance in the healthcare industry. Thus, while Gentry's construction of a FHE scheme based on ideal lattices was a stepping-stone in cryptography, its practical implementation met with efficiency bottlenecks, and its ability to solve real-world problems has not been realized.

Efficiency in HE is largely determined by the size of the cipher text and ensuring polynomial bounding to the security parameter, all through repeated computations.) Efficiency can be increased either by assuming circular security and implementing an expensive bootstrapping operation, or by extending the parameter sizes to enable a "levelled FHE" scheme which can evaluate circuits of large degree (e.g., exponential in the number of levels). To improve the efficiency of Gentry's scheme, Brakerski et al., took an unconventional approach by eliminating bootstrapping, basing security on weaker assumptions and relying on Learning With Error (LWE) or ring-LWE problem.

Although a great deal of effort has been applied to HE technology in recent years, it has become apparent that the technology is unlikely be used in more complicated settings requiring large amount of operations on data such as healthcare data. The reason may be that as the number of operations increase, the "noise" of the encrypted result also increases dramatically, which can render the operations impracticable with respect to time/cost or render the results error prone.

Further, there has yet to be a system that allows multiple computers to work together on homomorphic encrypted data (HE-data) in more mundane settings, for example, settings, in which computing devices each store its own data (e.g., each device has ownership of its data and other computers do not necessarily have rights to the data). The healthcare space is one such setting. In healthcare there can be multiple data custodians, each of which wishes to enforce patient privacy as well as protect its own data (e.g., with personal data encrypted using HE, data custodians can host the encrypted data without worrying about loss of privacy).

Secure Multi-party Computations (MPC) in applied cryptography deal with participants engaged in computing an end result, who cannot obtain information about another participant's input from the calculated outcome. In 1986, Yao paved the way to solve the MPC problem by introducing a two-party constant-round protocol. With the inclusion of FHE, new research efforts are making headway in solving the MPC problem using FHE. In various embodiments, distributed analytics models (with the inclusion of FHE) can allow third-party analytics companies to collaborate without disclosing consumer-patient data. In healthcare, secure MPC using FHE can greatly benefit patients, because healthcare providers, insurance and pharmaceutical companies work together to perform computations on encrypted data without compromising patient privacy. Although the FHE scheme is bandwidth efficient (since participant interaction is only necessary while providing input and retrieving output), it has computational limitations and considerable research effort is needed to improve its efficiency.

Although collective data analysis from different paradigms (e.g., social, genomic, financial, psychological etc.) can lead to a well-informed decision, security and privacy issues governed by legal compliance have compelled data custodians to restrict access to data in healthcare settings. With increased hesitancy to share data across healthcare clouds, HE in healthcare can facilitate breaking barriers to data sharing, creating new business models.

Further, it should be appreciated that analysis of healthcare data can have simple requirements; possibly including adding values, subtracting values, comparing values, and so forth. Although some very primitive HE systems exist (e.g., HElib, Pure Python Paillier Homomorphic Cryptosystem, etc.), they only offer a few primitive operators such as addition, subtraction, etc.; they do not offer insight into sharing data across computing devices.

System 10 is configured to address the above described issues (and others) in providing a system and method for homomorphic encryption in healthcare networks. According to various embodiments, HE can be extended to secure multi-party computation, with zero knowledge proofs and mix-nets (e.g., routing protocols that create hard-to-trace communications by using a chain of proxy servers that take in messages from multiple senders, shuffle them, and send them back out in random order to the next destination (possibly another mix node), breaking the link between the source of the request and the destination, making it harder for eavesdroppers to trace end-to-end communications). In a general sense, system 10 offers cloud-based access to healthcare data in encrypted database 32. According to various embodiments, system 10 can facilitate remote operations on the healthcare data in encrypted data 32; for example, consumer 34 can perform operations on the data in an encrypted manner irrespective of a location of consumer 34 with respect to cloud 14.

According to some embodiments, HE can be used on resource-constrained devices such as IoT devices to provide security measures to protect the data being stored and/or communicated. HE can be implemented by allowing the IoT devices to perform computations on encrypted data and by further extending privacy to functions, where operations on encrypted data are performed using encrypted functions. In various embodiments, the patient may be in complete control of personal healthcare data and data custodian 12 simply hosts the healthcare data encrypted using HE in encrypted database 32. In some embodiments, consumer 34 operated by advanced analytics companies can process the HE-data in a distributed manner.

According to various embodiments, system 10 can facilitate determining whether consumer 34 performs particular analytics operations on the encrypted data and whether the final recipient of the analysis results and/or data appropriately decrypts the analysis results and/or data from consumer 34 using Zero knowledge proof (ZNP). According to embodiments implementing ZNP, participants convince other participants of the validity or truthfulness of a mathematical statement, while imparting zero knowledge to the corresponding verifiers. In such cases, consumer 34 can convince the final recipient of the analysis operations by submitting ZNP that the necessary functions were computed and correspondingly, the final recipient can prove to consumer 34 in ZNP that the final encrypted outcome was decrypted in an appropriate manner. In some embodiments, non-interactive ZNP may be minimized using FHE.

In an example scenario, consider a pharmaceutical company that is investigating an experimental drug. The drug trial and testing process includes recruiting patients, who may have complex and potentially interacting medical conditions. Before administering the drug, concomitancy (e.g., patient already on medication that may interact with the experimental drug) and comorbidity (e.g., patient has more than one health condition, and the experimental drug alleviates one of the health condition to the detriment of another health condition) may be known for a patient, but is restricted information. Existing software applications in the healthcare marketplace do not have sufficient coverage for such patients. However, embodiments of system 10 can provide real-time cloud service across all stakeholders to enable analysis of healthcare data related to the patients in the trial. Such types of analysis services on HE data can be useful in treating rare diseases, applicable across all diseases. In some embodiments, the service represents a global registry for information related to the rate disease. HE allows analysis on the data without sacrificing privacy.

Turning to the infrastructure of system 10, data custodian 12 can be embodied as computer executable instructions stored on one or more non-transitory computer-readable media (e.g., hard drives, optical storage media, flash drives, ROM, RAM, etc.) that, when executed by one or more processors, cause the processors to execute the functions and processes described herein. In some embodiments, data custodian 12 can be integrated into a single computing device or distributed among a plurality of computing devices (either locally or remotely located from one another) communicatively coupled via data exchange interfaces (e.g., short-range, long-range, wireless, optical, wired, near-field communication, Bluetooth, Ethernet, Wi-Fi, USB, etc.), and/or connected via local or long-range networks (e.g., Internet, cellular, local-area networks, wide-area networks, intranets, etc.). In some embodiments, data custodian 12 can be embodied as one or more dedicated hardware computing devices specifically programmed (e.g., via firmware) to execute the functions and processes described herein. Note that although only one data custodian 12 and consumer 34 is illustrated in the figure for simplicity, any number of data custodians and consumers may be included in system 10 within the broad scope of the embodiments.

In some embodiments, cOS 16 may execute in a distributed manner over myriad servers and other computing devices in cloud 14. cOS 16 integrates clinical, financial, operational and environmental data into a single platform. cOS 16 comprises a cloud-based platform for patient records, medical devices, imaging systems, financial systems, costing systems, evidence-based clinical pathways, and personalized genomic and proteomic data. cOS 16 integrates data from existing systems, such as electronic medical records (EMRs), labs and pathology, imaging systems (PACS and RIS), pharmacy databases, and medical devices (including in-home devices). In various embodiments, cOS 16 comprises a plurality of self-contained modules that can accept data in different formats and convert the data into a uniform format.

Figure 2:
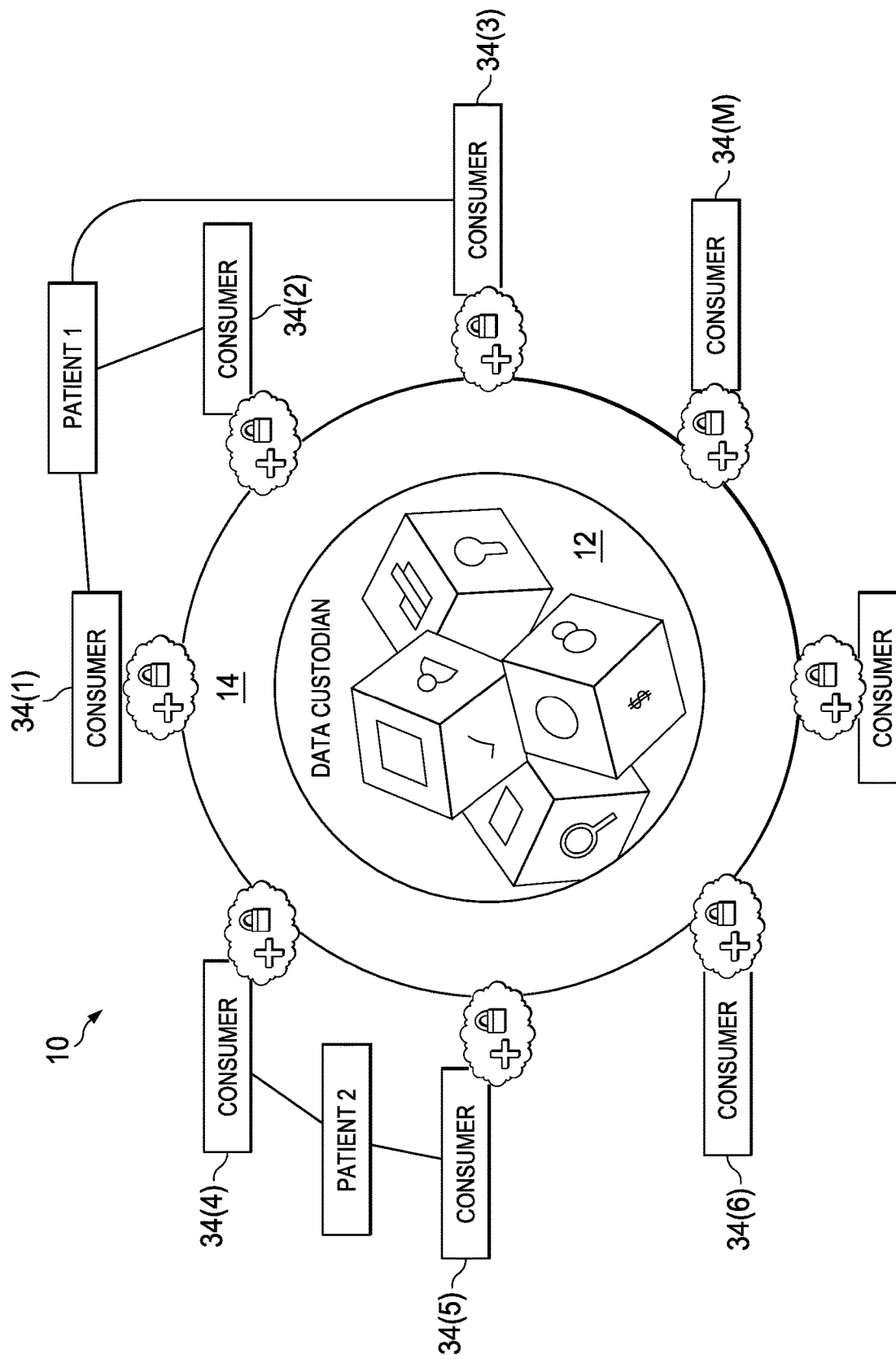
FIG. 2 is a simplified block diagram illustrating example details of the system according to an embodiment.

Turning to FIG. 2, FIG. 2 is a simplified block diagram illustrating example details of an embodiment of system 10. Consumers 34(1)-34(M) may access data custodian 12 over cloud 14. One should appreciate that each of consumers 34(1)-34(M) represents a computing device. Each consumer 34(1)-34(M) may be provided with unique cryptographic keys to access and operate on encrypted data at data custodian 12. Consumers 34(1)-34(M) may operate on the encrypted data according to permissions from patients (e.g., patient 1 allows consumers 34(1)-34(3) to perform certain operations on patient 1's data; patient 2 allows consumers 34(4)-34(5) to perform certain operations on patient 2's data; and so on). In some embodiments, patient 1 may allow access permissions to a first portion of patient 1's encrypted data to consumer 34(1); patient 1 may allow access permissions to a different second portion of patient 1's encrypted data to consumer 34(2); patient 1 may allow access permissions to a still different third portion of patient 1's encrypted data to consumer 34(3); and so on, with each consumer being provided access to a different portion of the encrypted data.

In various embodiments, the data owners of individual pieces of data stored at data custodian 12 may have complete control over who accesses the data. For example, a consumer-patient's clinical, financial, genomic, social, environmental data, etc. can reside with their respective data custodians, but the patient will have the final authority to decide which analytics company performs analytics on his or her data.

In an example scenario encompassed by embodiments of system 10, assume that the encrypted data is hosted by data custodian 12 and the data owner (e.g., patient 1) wants to retrieve a holistic healthcare portfolio. Patient 1 can request data custodian 12 to share the appropriate portion of the encrypted data to specific third-party analytics companies that operate consumers 34(1)-34(3). Subsequently, the analytics companies run HE (e.g., Bayesian inference) on encrypted healthcare data and collectively predict a holistic health score (e.g., considering factors from other paradigms and not limiting to social, clinical, behavioral, psychological, environmental, genomic, financial, etc.). The encrypted output is sent back to patient 1 to decrypt and learn about the outcome (e.g., a holistic health score in the healthcare domain). Such a model would preserve the privacy of the patients who can decide the level of exposure they are willing to authorize.

Embodiments of system 10 can facilitate widespread acceptance of HE in the healthcare cloud industry, potentially leading to a new platform for designing and developing advanced analytics solutions. For example, ease of access to HE-data, which can be significantly large in volume, can lead to development of predictive algorithms having higher accuracy. The ability to perform complex computations on encrypted data expands the horizon for distributed data analytics, including predictive analytics. In another example, encrypted big data cloud hosted in the United States can be used for predictive analytics to treat a patient elsewhere in the word such as in Africa, or vice versa. For example, consumers 34(4) and 34(5) may be located in Australia; data custodian 12 may be located in the United States; and so on.

Furthermore, predicting an epidemic by executing predictive analytics models on various encrypted data (e.g., genetic data associated to a parasite population) in cloud 14 can swiftly provide new insights to medical researchers to discover an appropriate remedy and save millions of lives. In various embodiments, homomorphic encrypted big data clouds, such as cloud 14, can provide endless opportunities for healthcare providers and analytics companies to perform advanced analytics on data across the globe and improve global population health.

Embodiments of system 10 provide a HE model that protects data privacy stored at data custodian 12 and obfuscates operations performed on the ciphered data. Embodiments of system 10 can provide anonymized analytics by not disclosing any function or operation on data custodian 12. The anonymized operations may also be authenticated, for example, to prevent a Denial of Service (DoS) attack.

Figure 3:
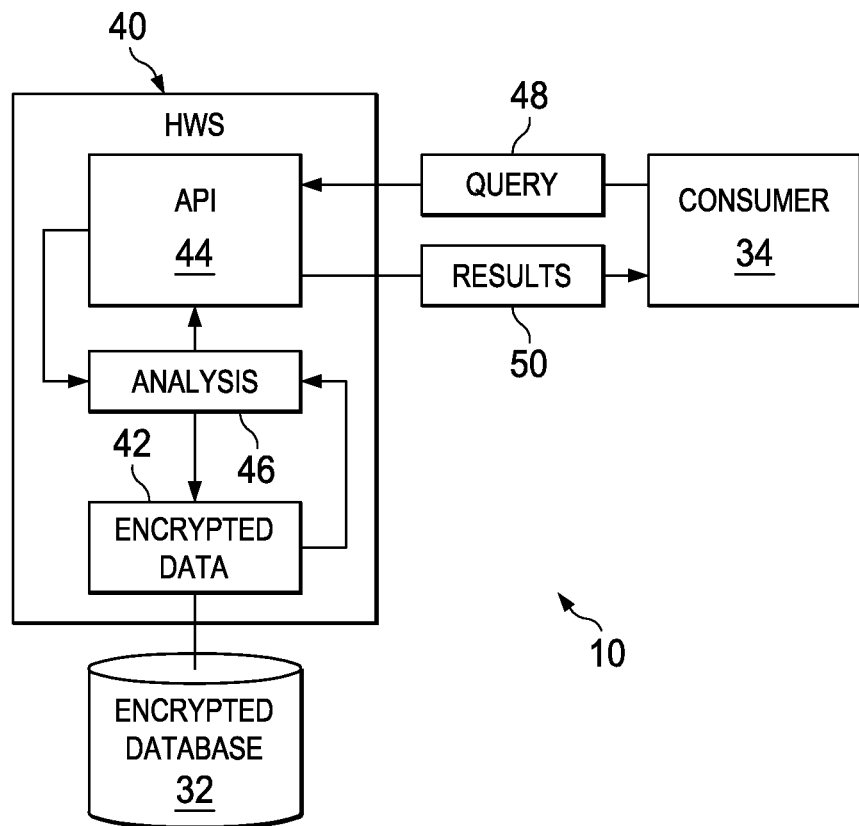
FIG. 3 is a simplified block diagram illustrating other example details of the system according to an embodiment.

Turning to FIG. 3, FIG. 3 is a simplified diagram illustrating example details of a HWS 40 according to an embodiment of system 10. In various embodiments, data custodian 12 creates and owns a homomorphic work space (HWS) 40 and has access to data in encrypted database 32. Data custodian 12 may have a secret key to HWS 40 and provide a corresponding public key to consumer 34. In a general sense, data custodian 12 does not know what operations will be performed on the healthcare data in encrypted database 32. In various embodiments, consumer 34 performs various operations on certain encrypted data 42 in encrypted database 32. Consumer 34 can access and be allowed to use encrypted data 42 based in part on authentication and authorization through the public key.

In some embodiments, data custodian 12 constructs HWS 40 and provides access thereto via an API 44. API 44 enables consumer 34 to consult encrypted data 42, determines if encrypted data 42 is reasonable for use, and converts encrypted data 42 to usable form for consumer 34. In a general sense, API 44 is not aware of the location of encrypted data 42, or any actual values of encrypted data 42.

In various embodiments, HWS 40 represents a memory area (e.g., memory locations such as memory addresses). HWS 40 may be instantiated (e.g., created, generated, etc.) when a HW session is initiated. Any query from consumer 34 for certain encrypted data 42 is translated by API 44, which causes the requested encrypted data 42 to be pulled up from encrypted database 32 and inserted into the memory area represented by HWS 40. Various analysis 46 (e.g., digital and/or mathematical operations, algorithms, etc. in encrypted form) may be performed on the memory contents. The results of analysis 46 may be returned to consumer 34. At the end of the HW session, HWS 40 may be closed out.

In some embodiments, HWS 40 can build on top of HE primitives from commonly available HE libraries (HELib; see URL github.com/shaih/HElib). The primitives may be included in API 44. For example, the HE primitives of negation and addition can be combined to create a subtraction operator. In some embodiments, HWS 40 may comprise a virtual memory space distributed across one or more memory locations possibly across networking nodes. In some embodiments, HWS 40 may be instantiated and the query requirements mapped to HWS 40. In other embodiments, HWS 40 may correspond to a HE file system, including a namespace manager and HE operating system (HEOS). Note that any known mechanism for implementing homomorphic encryption can be included in the broad scope of the embodiments. Merely as an example, and not as a limitation, the disclosure of U.S. Pat. No. 8,565,435 to Gentry et al., titled "Efficient Implementation of Fully Homomorphic Encryption" is incorporated herein in its entirety.

Embodiments of system 10 may facilitate a fast response time, with a query parser placing operations as close to data as possible (or vice versa). In some embodiments, HWS 40 may be comprised in a network architecture that enables integration and interoperation across connected products. In a general sense, the HE space represented by HWS 40 creates "noise" that makes it difficult to decrypt. Increasing number of computations induces greater security, because of the increased difficulty in decrypting the final result of the computations. However, a balance may be desired between practicality of computation and the signal to noise (e.g., some computations become impractical due to dealing with the large noise). Haskell language library or similar techniques can specify computational requirements for HWS 40 that may be included in various embodiments of system 10.

During operation, consumer 34 sends a query 48 to data custodian 12. Data custodian 12 constructs a Homomorphic Work session (HW session) for query 48 and instantiated HWS 40. In some embodiments, the HW session comprises an asymmetric cryptographic session based on algorithms that require two separate keys that are mathematically linked, one of which is secret (or private) and one of which is public. The public key is used to encrypt plain text and the private key is used for the opposite operation, in these examples to decrypt cipher text. In some embodiments, the HW session comprises a symmetric cryptographic session based on algorithms that use the same key to encrypt plain text and decrypt cipher text.

Data custodian 12 creates a query-specific vector space with V =vector of encrypted data 42 related to or in response to query 48. V[i] is the value for each element i in the vector space. In a general sense, V can be considered a "form" (e.g., record) and V[i] can be considered a field of a record, with i being the address of the value for the specific field. The value of i can range from 0 to n where n is the number of elements in the vector.

Each member V[i] has a well-defined attribute that corresponds to i and value V[i], thus forming an attribute-value pair. Note that the attributes correspond to an a priori defined name space. In some embodiments, each attribute is assigned an index for the HW session, for example, 0=First name, 1=Middle name, 2=Last name, etc.; j=Temperature; k=International Classification of Disease (ICD) code; n=last item in list; and so on. The elements of the vector space can be blank or defined for future use. The attribute can be mapped to an index, with an action on the value converted from the index. Note that the index is more than a hash table, implementing HE algorithms therein. API 44 may allow for various primitives, such as Add, Subtract, Multiply, Divide, Compare, Zero, One, Insert, Delete, etc., that can produce valuable (e.g., non-trivial) results 50 on encrypted data 46. Results 50 are returned to consumer 34 in response to query 48.

In various embodiments, analysis 46 may comprise encrypted analysis, such as using fully homomorphic encryption (FHE). The FHE scheme can enable various analysis, which can be executed on encrypted data 42 to produce an encryption of the result, comprising results 50. In an example embodiment, query 48 may comprise a request associated with a holistic healthcare portfolio of a particular patient. The holistic healthcare portfolio may include medical data, financial data, social data, environmental data, genomic data, and virtually any other data available in encrypted database 32 and associated with the health or wellbeing of the particular patient and to which the particular patient has provided access to consumer 34. The data relevant to the holistic healthcare portfolio may be extracted from encrypted database 32 and compiled into encrypted data 42, comprising the results set corresponding to the query (i.e., V[i]). Using API 44, FHE analysis 46 may be computed on encrypted data 42. Analysis 46 may comprise determining a holistic health score of the particular patient. The holistic health score may be output as results 50. The holistic health score may be encrypted using appropriate cryptographic keys associated with the HW session and provided to consumer 34, which can decrypt the holistic health score using the cryptographic keys of the HW session.

In some embodiments, HWS 40 may be instantiated at only data custodian 12. In such embodiments, consumer 34 merely receives analysis results 50 and does not perform any analysis on encrypted data 42. In other embodiments, HWS 40 may be instantiated at consumer 34 in addition to data custodian 12. In such embodiments, certain analysis 46 may be performed at data custodian 12 and certain other analysis may be performed at consumer 34. For example, data custodian 12 may generate a structured encrypted vector $V_{ct}$ from an unstructured collection of information V in encrypted data 42. The encrypted vector $V_{ct}$ and API 44 may be sent to consumer 34. Consumer 34 may store a local copy of $V_{ct}$ and locally analyze $V_{ct}$ using API 44 received from data custodian 12. The local copy of $V_{ct}$ and API 44 instantiated in consumer 44 may comprise the local copy of HWS 40 at consumer 34. In yet other embodiments, HWS 40 may be instantiated only at consumer 34. In such embodiments, data custodian merely transmits encrypted data 42 and does not perform any analysis on encrypted data 42.

Figure 4:
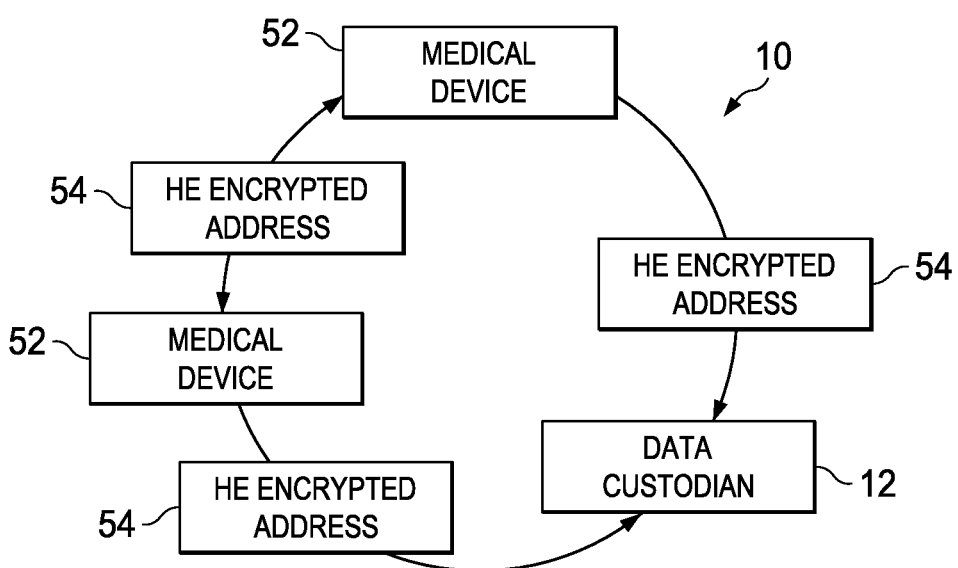
FIG. 4 is a simplified block diagram illustrating yet other example details of the system according to an embodiment.

Turning to FIG. 4, FIG. 4 is a simplified block diagram illustrating example details of a topology hiding protocol according to an embodiment of system 10. In some embodiments, topology hiding protocol with HE on packet headers may be implemented, for example, for communication to and from IoT devices, such as medical devices 52, to prevent security lapses such as distributed denial of service (DDos). Medical devices 52 can include wearable sensors, such as fitness trackers, or medical sensors that can communicate over a network (e.g., blood pressure sensor configured with a wireless transmitter).

Medical devices 52 may be configured with appropriate network interfaces with HE modules that can encrypt packet header information. In an example embodiment, the source address of medical devices 52 may be encrypted using HE; thus, botnets may not be able to find the original address, and a DDoS attack can be mitigated by forwarding all malicious traffic to a sinkhole. Packets subject to the HE may indicate a conventional destination address (e.g., corresponding to another medical device 52, or data custodian 12), and HE encrypted source address 54. Network nodes (e.g., switches and routers) encountering the packets may also be configured with appropriate HE modules that can interpret the source address based on cryptographic key exchanges between the network nodes and the sending medical devices 52. The HE may be implemented on communication among medical devices 52 and also between medical devices 52 and data custodian 12, so that packets traversing between medical devices 52 configured with HE adapted topology hiding protocol may be secure and private.

Figure 5:
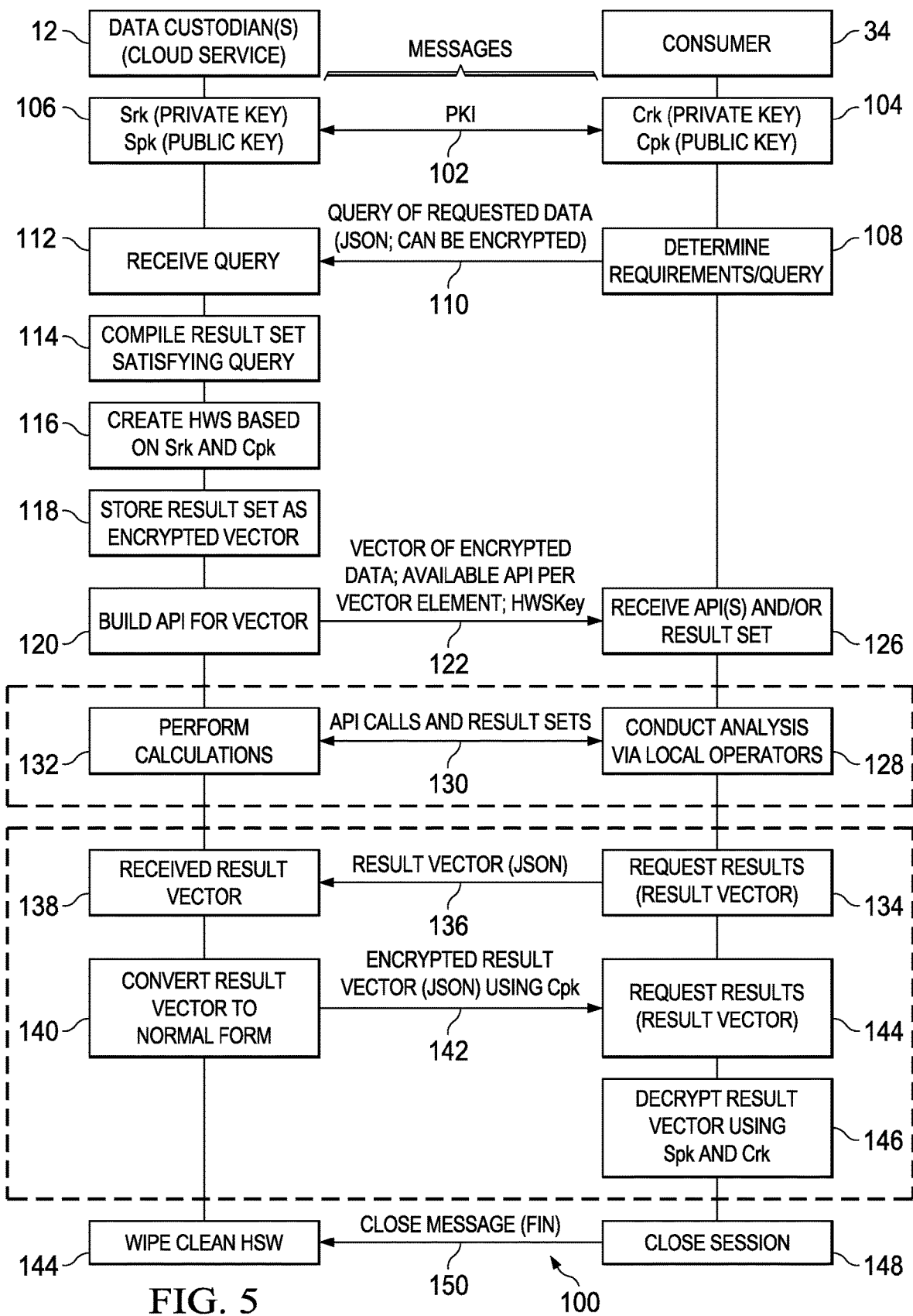
FIG. 5 is a simplified sequence diagram illustrating example operations that may be associated with an embodiment of the system.

Turning to FIG. 5, FIG. 5 is a simplified sequence diagram illustrating example operations 100 that may be associated with an embodiment of system 10. According to embodiments of system 10, multiple computers may share and operate on HE data, while also keeping the data private. Of specific note, the disclosed technique separates knowledge of the data and knowledge of the operations performed on the data. Data custodian 12 offers access to data within a purpose-built HW session. A computer client comprising consumer 34 may wish to consume the data and operate on the data, but does not necessarily have rights to the data.

Data custodian 12 executing in a server in cloud 14 has access to the desired healthcare data. However, the server does not know what operations are desirable to consumer 34 executing on the client. The client does not have access to the healthcare data due to the HWS configuration of system 10. Moreover, the client need not necessarily know a priori what operations it wishes to perform. For example, the operations may depend on the data available at data custodian 12. Thus, the data is fundamentally separated from the operations that will be performed on the data, thereby isolating the two systems, at least to a degree, as desired by the stakeholders (e.g., data owner, data custodian 12, patient, doctor, insurance company, etc.).

Consumer 34 wishes to access the healthcare data stored at data custodian 12. The two entities begin their shared operation by conducting a key exchange 102, which can be performed using known PKI infrastructure. For example, consumer 34 has a public/private key pair $C_{pk}/C_{rk}$ 104 and data custodian 12 also has a corresponding public/private key pair $S_{pk}/S_{rk}$ 106. During key exchange 102, both sides obtain the public key of the other thereby allowing each to send encrypted data to the other in a secure fashion. Key exchange 102 can be considered as an initial handshake for constructing the HW session. From this point on, communications between consumer 34 and data custodian 12 can take place over a secure link (e.g., SSL, SSH, HTTPS, etc.) based on the one or more implementations of cryptographic algorithms (e.g., AES, 3DES, etc.) and the exchanged keys. Both data custodian 12 and consumer 34 can conduct their operations within a secure container (e.g., virtual machine, Docker™ container, run time, etc.) to ensure that data and processes remain isolated from other data or other processes that might be present on the respective devices.

In the example shown, consumer 34 begins the exchange in the HW session by formulating query 48 targeting certain encrypted data 42 at data custodian 12 at 108. Query 48 (e.g., SQL, key words, search terms, etc.) could be complementary to the data schema supported by data custodian 12. It should be appreciated that consumer 34 could have an understanding of the type of data available at data custodian 12. For example, consumer 34 might be provisioned with a schema of data at data custodian 12. Alternatively, consumer 34 could formulate an unstructured keyword query similar to the queries that can be submitted to a public search engine over the Internet. At 110, consumer 34 sends query 48 to data custodian 12. In various embodiments, query 48 may be encrypted appropriately.

Data custodian 12 receives query 48 and decrypts it at 112. Data custodian 12 uses query 48 to consult encrypted database 32 of healthcare records to generate, at 114, a result set that includes zero or more entries that are considered to satisfy query 48. The result set could be a set of uniformly formatted records or unstructured documents. If the documents are unstructured, data custodian 12 can filter the result set to create a structured result set that is amenable for use in HWS 40.

Of specific interest, the result set can be compiled in the form of a vector. For example, consumer 34 might request the blood pressure of all people taking a particular drug. The result set can be a vector (e.g., list), in which each member of the vector is a blood pressure for a specific patient; the vector comprises a set of numbers representing the blood pressures of multiple patients taking the drug; the vector only has a single type of data, numbers or integers in this case. The vector could also include more than numbers. Each member of the vector could represent other types of values, such as diagnostic codes, procedure codes, names of diseases, strings, names, etc. In such cases, the vector can be a representation of data where each index of the vector corresponds to a specific dimension of a namespace, where each member has a value for the corresponding dimension. As mentioned previously, the index and value (i.e., V[i]) can represent attribute-value pairs.

As an example, consider that V[i] is the vector where the index i runs from 0 to n, V[0] could include temperature, V[1] might include an ICD-10 code, up through V[n]. One should note that data custodian 12 can define each dimension during construction of the vector. The dimension of the vector can be defined based on the purpose or specific needs of the HW session; based on metadata in query 110 for example. In other words, the dimension of the vector can be defined in real-time as data custodian 12 builds the vector to satisfy query 48. In some scenarios, a table of values would serve as a better result set than just a single vector. In such cases, the table of values can comprise multiple vectors. Data custodian 12 can also compile a list of the meaning of each dimension, which can be conveyed to consumer 34. In some cases, the vector can include different or heterogeneous types of data, in which case the vector could be considered one row of a table or spreadsheet. In other cases, the vector can include the homogeneous or the same type of data, which could be considered one column of the table or spreadsheet.

Data custodian 12 continues by instantiating HWS 40 at 116. Instantiating HWS 40 can include creating an HE context with a key, for example as described in U.S. Pat. No. 8,565,435 to Gentry et al., which is incorporated herein in its entirety. An HWS key (HWSKey) can be generated by using data custodian 12's secret key ($S_{rk}$) and consumer 34's public key ($C_{pk}$). The key be accessible by both data custodian 12 and consumer 34, for example, so that both entities can conduct analysis 46 on encrypted data 42. The vector of data can then be converted to cipher text, for example, using HE primitives from HElib. The context can be specific to the HW session between data custodian 12 and consumer 34, via the keys. The vector V can become cipher text vector $V_{ct}$ having the same number of elements as V. Each element, however, has a corresponding encrypted value rather than the original, unencrypted value. Data custodian 12 may store the result set as encrypted vector $V_{ct}$ at 118.

Note that data custodian 12 does not necessarily know a priori the nature of $V_{ct}$ until the result set is compiled. More specifically, data custodian 12 does not know the number of elements that $V_{ct}$ will have or what the data means until the result set is compiled. The HE operations that may be used during the HW session to analyze $V_{ct}$ may not be known apriori by either data custodian 12 or consumer 34.

In an example embodiment, at 120, data custodian 12 constructs or builds one or more of API 44 that can be used to operate on encrypted data 42 (e.g., members of WO according to the data type or types supported by encrypted data 42 (e.g., $V_{ct}$[i]). API 44 can be constructed in the form of methods of an instantiated class of $V_{ct}$, for example. In the case where $V_{ct}$ represent numbers, API 44 can include instructions to support mathematical operations, such as addition, subtraction, multiplication, negations, etc. Other data types could include other supported operations in API 44, such as compare, increment, decrement, sort, etc., that can be built on the HE primitives of the HElib as an example.

Depending on the security level required (and potentially other parameters of interest), higher order operations can be restricted or locked out to consumer 34 to ensure that actual values of data are not derivable from $V_{ct}$ (in other words, that V cannot be back-calculated from $V_{ct}$). For example, consumer 34 could be restricted from using a compare operator (e.g., >, <, =, etc.) that could potentially indicate the actual value of $V_{ct}[i]$ by comparing cipher texts of known values to that of $V_{ct}[i]$. One aspect of the embodiments of system 10 is considered to include tagging HE operators with access control list information so that only authorized external agents (e.g., consumer 34) have access to such operators.

In various embodiments, HWS 40 is instantiated in the form of the context (e.g., HWSkey, etc.), session (e.g., SSL, TCP/IP, etc.), $V_{ct}$ (embodying encrypted data 42) and API 44. Data custodian 12 can transmit the vector of encrypted data along with available API 44 to consumer 34 at 122, subject to authorization or permissions. Note that consumer 34 can use the transmitted data to re-instantiate a local copy of the $V_{ct}$ along with associated methods. For example, data custodian 12 can serialize an instance of $V_{ct}$ via XML, JSON, YAML, Binary XML, HDF, netCDF, GRIB, or other serialization formats. Consumer 34 could instantiate its local copy within a secured container (e.g., virtual machine, Docker container, etc.), which can be bound to HWS 40 (or the HW session, as applicable).

In some embodiments, at 128, consumer 34 may perform analysis 46 using API 44 locally. For example, consumer 34 calls the supported APIs to operate on the cipher text of V. In some embodiments, API 44 may be generic and may require using the HWSkey as an input thereto. In other embodiments, API 44 may be constructed with the knowledge of the HWSkey already incorporated into their construction, for example, where consumer 34 has restricted access to operators or $V_{ct}[i]$ values. This approach is considered advantageous because API 44 for $V_{ct}$ would be bound specifically to consumer 34 via the HWSkey. Other agents would not be able to invoke API 44 because they would not be able access the APIs via their own public or private key. Note that consumer 34 operates on encrypted data 42 locally without knowing the values of encrypted data 42 or even the results of the analysis. Further, data custodian 12 does not know what operations are being executed.

Although the disclosure herein indicates that consumer 34 can operate on encrypted data 42 locally, it should be appreciated that API 44 could represent remote procedure calls where operations take place remotely on data custodian 12, as at 130. In such embodiments, data custodian 12 could offer a web service "notebook" through which consumer 34 operates on encrypted data 42 by submitting calls to supported API 44. At 132, calculations (e.g., analysis 46) may be performed at data custodian 12. Data custodian 12 can record, if allowed, the HW session as a workbook with access permitted only to the results of analysis 46 upon request by consumer 34 at 134. Note that in some embodiments, encrypted analysis 46 prevents consumer 34 from deciphering encrypted data 42 or V.

In view that consumer 34 is analyzing (e.g., operating on) cipher text and that the analysis results are in cipher text, consumer 34 would likely require a technique for obtaining the results in clear text. According to an example embodiment, at 134, consumer 34 computes results vector 36, which comprise cipher text. At 136, consumer 34 sends results vector 36 back to data custodian 12. Data custodian 12 receives results vector 36 at 138 and at 140 decrypts results vector 36 to normal form. The reader is reminded that the normal form of the result are stored in the memory of the secure container within data custodian 12, thereby protecting the decrypted result set from unauthorized access by other processes executing on data custodian 12.

At 142, data custodian 12 and sends the decrypted normal form results vector 36 back to consumer 34 in an encrypted format that consumer 34 can decrypt using its private key. Note that the encryption for transmission to consumer is performed using security keys associated with the homomorphic work session. In other words, the transmitted data is encrypted so that third parties cannot directly observe the data, but can be decrypted by the parties to the exchange. Note that this is in contrast to the encrypted results vector 36 itself, which can be decrypted only at data custodian 12 using implementations of appropriate homomorphic algorithms. In various embodiments, consumer 34 may generate interesting data from secured data without ever knowing what the secured data is. At 144, consumer 34 may receive encrypted normal form results vector 36. At 146, consumer 34 may decrypt encrypted normal form results vector 36, for example, using the keys used to create the HW session.

As an example, consider a case where $V_{ct}$ comprises a set of patient weights that are taking a specific drug. Consumer 34 is not permitted to have the actual weight values. Still, consumer 34 could perform operations such as sum over all the weights and take an average. The result could comprise a single value: the average, or multiple values: the average, mean, mode, standard deviation, etc. The results would be encrypted in HWS 40. Consumer 34 could send the result vector back to data custodian 12, who then returns decrypted results back to consumer 34. It should be appreciated that data custodian 12 could conduct the decryption within its own secure container so that the data is deleted from data custodian's memory when the HW session ends.

When consumer 34 is finished or satisfied with the results at 140, it can send a close message (FIN) to data custodian 12 to terminate the HW session at 142. Data custodian 12 may clear its memory cache of HWS 40 at 144 and tear down any virtual machines, containers, or delete V.

In some embodiments, the architecture of system 10 can be configured to support noise management. As system 10 operates on cipher text using increasingly complex operators (e.g., multiplication, division, etc.), the cipher text generates greater noise. The noise has two impacts. First, the time to complete an operation increases. Second, the noise can exceed the threshold capability of the underlying implementation of the homomorphic algorithm to properly propagate valid information. In other words, the excessive noise causes the homomorphic algorithms to generate errors.

In various embodiments, noise can be mitigated through renormalization. As the noise level of $V_{ct}$ or its result vectors increases, consumer 34 (and/or data custodian 12) can choose to have the results renormalized. For example, consumer 34 could have a set of noisy results that it wishes to keep from data custodian 12. Consumer 34 can decrypt the noisy results back to plain text, and then generate a new encrypted result vector using a new (or next) HWSkey. Consumer 34 could submit the HWSkey back to data custodian 12, which in turn can renormalize the original $V_{ct}$ based on the new HWSkey or context. Now, both the $V_{ct}$ and the results have less noise within the same newly created encrypted space of HWS 40. It should be noted that renormalization can be constructed to respect privacy to ensure data remains segregated between different data owners, contexts, policies, etc. Data custodian 12 and consumer 34 could establish new HWSkeys that keep each stakeholder's data private appropriately based on particular needs.

It should be apparent to those skilled in the art that many more modifications besides those already described are possible without departing from the scope of the embodiments disclosed herein. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The foregoing discussion provides many example embodiments of systems and methods for alarm fatigue management. Although each embodiment represents a single combination of various elements, all possible combinations of the disclosed elements are intended to be included in the broad scope of the disclosure. Thus if one embodiment comprises elements A, B, and C, and a second embodiment comprises elements B and D, then the scope of the disclosure is considered to include other remaining combinations of A, B, C, or D, even if not explicitly disclosed.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary. Note that any recitation of ranges of values herein is merely intended to serve as a shorthand method of referring individually to each separate value falling within the range. Unless otherwise indicated herein, each individual value is incorporated into the specification as if it were individually recited herein.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In some embodiments, the numbers expressing quantities of ingredients, properties such as concentration, reaction conditions, and so forth, used to describe and claim certain embodiments of the various embodiments described herein are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of system 10 are approximations, the numerical values set forth in the specific examples are reported as precisely as practicable. The numerical values presented in some embodiments of system 10 may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the various embodiments and does not pose a limitation on the scope of the various embodiments otherwise claimed. No language in the specification should be construed as indicating any non-claimed element essential to the practice of the various embodiments disclosed herein.

Groupings of alternative elements or embodiments of the various embodiments of system 10 disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments. The use of any and all examples, or exemplary language (e.g., "such as") provided with respect to certain embodiments herein is intended merely to better illuminate the invention and does not pose a limitation on the scope of the embodiments otherwise claimed. No language in the specification should be construed as indicating any non-claimed essential.

In example implementations, at least some portions of the activities outlined herein may be implemented in software in, for example, data custodian 12. In some embodiments, one or more of these features may be implemented in hardware, provided external to these elements, or consolidated in any appropriate manner to achieve the intended functionality. The various network elements may include software (or reciprocating software) that can coordinate in order to achieve the operations as outlined herein. In still other embodiments, these elements may include any suitable algorithms, hardware, software, components, modules, interfaces, or objects that facilitate the operations thereof.

Furthermore, data custodian 12 and various other components described and shown herein (and/or its associated structures) may also include suitable interfaces for receiving, transmitting, and/or otherwise communicating data or information in a network environment. Additionally, some of the processors and memory elements associated with the various nodes may be removed, or otherwise consolidated such that a single processor and a single memory element are responsible for certain activities. In a general sense, the arrangements depicted in the FIGURES may be more logical in their representations, whereas a physical architecture may include various permutations, combinations, and/or hybrids of these elements. It is imperative to note that countless possible design configurations can be used to achieve the operational objectives outlined here. Accordingly, the associated infrastructure has a myriad of substitute arrangements, design choices, device possibilities, hardware configurations, software implementations, equipment options, etc. Moreover, all methods described herein can be performed in any suitable order unless otherwise indicated herein or otherwise clearly contradicted by context.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some of example embodiments, one or more memory elements (e.g., memory element 24) can store data used for the operations described herein. This includes the memory element being able to store instructions (e.g., software, logic, code, etc.) in non-transitory media such that the instructions are executed to carry out the activities described in this Specification. These devices may further keep information in any suitable type of non-transitory storage medium (e.g., random access memory (RAM), read only memory (ROM), field programmable gate array (FPGA), erasable programmable read only memory (EPROM), EEPROM, etc., software, hardware, or in any other suitable component, device, element, or object where appropriate and based on particular needs.

A processor can execute any type of instructions associated with the data to achieve the operations detailed herein in this Specification. In one example, processors (e.g., processor 22) could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., a field programmable gate array (FPGA), an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

The information being tracked, sent, received, or stored in system 10 could be provided in any database, register, table, cache, queue, control list, or storage structure, based on particular needs and implementations, all of which could be referenced in any suitable timeframe. Any of the memory items discussed herein should be construed as being encompassed within the broad term 'memory element.' Similarly, any of the potential processing elements, modules, and machines described in this Specification should be construed as being encompassed within the broad term 'processor.'

It is also important to note that the operations and steps described with reference to the preceding FIGURES illustrate only some of the possible scenarios that may be executed by, or within, the system. Some of these operations may be deleted or removed where appropriate, or these steps may be modified or changed considerably without departing from the scope of the discussed concepts. In addition, the timing of these operations may be altered considerably and still achieve the results taught in this disclosure. The preceding operational flows have been offered for purposes of example and discussion. Substantial flexibility is provided by the system in that any suitable arrangements, chronologies, configurations, and timing mechanisms may be provided without departing from the teachings of the discussed concepts.

It should also be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, random access memory (RAM), flash memory, read-only memory (ROM), etc.). The software instructions can configure a suitable computing device to provide the roles, responsibilities, or other functionality as discussed herein with respect to the disclosed apparatus. In some embodiments, the various servers, systems, databases, or interfaces exchange data using standardized protocols or algorithms, possibly based on hyper-text transfer protocol (HTTP), hyper-text transfer protocol secure (HTTPS), Advanced Encryption Standard (AES), public-private key exchanges, web service application programming interfaces (APIs), known financial transaction protocols, or other electronic information exchanging methods. Data exchanges preferably are conducted over a packet-switched network, the Internet, local area network (LAN), wide area network (WAN), virtual private network (VPN), or other type of packet switched network.

As used in the description herein and throughout the claims that follow, when a system, engine, server, device, module, or other computing element is described as configured to perform or execute functions on data in a memory, the meaning of "configured to" or "programmed to" refers to one or more processors or cores of the computing element being programmed by a set of software instructions stored in the memory of the computing element to execute the set of functions on target data or data objects stored in the memory.

One should appreciate that the disclosed techniques provide many advantageous technical effects including reduction in latency between a computing device ingesting healthcare data and generating a prediction or recommendation. Latency is reduced through storage of health care data in a memory and in the form of N-grams, which can be computationally analyzed quickly.

Although the present disclosure has been described in detail with reference to particular arrangements and configurations, these example configurations and arrangements may be changed significantly without departing from the scope of the present disclosure. For example, although the present disclosure has been described with reference to particular communication exchanges involving certain network access and protocols, system 10 may be applicable to other exchanges or routing protocols. Moreover, although system 10 has been illustrated with reference to particular elements and operations that facilitate the communication process, these elements, and operations may be replaced by any suitable architecture or process that achieves the intended functionality of system 10.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) or paragraph (f) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

What is claimed is:

1. A computer-implemented method of providing access to an encrypted result set, the method comprising:
    creating a homomorphic encryption (HE) context among at least two computing devices;
    instantiating, at least in part based on the HE context, a homomorphic work space (HWS) in a non-transitory, computer readable first memory of a first computing device of the at least two computing devices, wherein the HWS is distributed among the at least two computing devices;
    loading encrypted data into the first memory, wherein the encrypted data is encrypted according to the HE context and wherein the first computing device lacks access to an unencrypted version of the encrypted data;
    generating an encrypted result set in the first memory by executing at least one homomorphic operation on at least a portion of the encrypted data according to instructions from a second computing device of the at least two computing devices;
    serializing at least the encrypted result set as a serialized object;
    transmitting, over a network, the serialized object including at least the encrypted result set to the second computing device.

2. The method of claim 1, further comprising establishing a secure communication link over the network between at least the first and the second computing device.

3. The method of claim 1, wherein the encrypted result set comprises an encrypted result vector.

4. The method of claim 3, wherein the encrypted result vector represents one or more attribute-value pairs responsive to a set of operations including the at least one homomorphic operation.

5. The method of claim 1, wherein the serialized object comprises a binary object.

6. The method of claim 1, wherein the serialized object comprises a JSON object.

7. The method of claim 1, wherein the HWS comprises a learning with errors (LWE) environment.

8. The method of claim 1, wherein the HWS comprises a lattice cryptographic environment.

9. The method of claim 1, wherein the HWS comprises a fully homomorphic encryption (FHE) environment.

10. The method of claim 1, wherein the at least one homomorphic operation comprises a polynomial function.

11. The method of claim 1, wherein the first computing device is part of a homomorphic cloud-based service.

12. The method of claim 11, wherein the homomorphic cloud-based service comprises a community cloud service.

13. The method of claim 1, further comprising terminating the HWS by sending a close message to the first computing device from the second computing device.

14. The method of claim 1, wherein the HE context is associated with at least one corresponding HWS key.

15. The method of claim 1, wherein the HWS comprises at least one secure container.

16. The method of claim 1, further comprising restricting access to the at least one homomorphic operation to the second computing device.

17. The method of claim 1, further comprising reducing noise associated with the encrypted result set and introduced by execution of the at least one homomorphic operation on the encrypted data.

18. The method of claim 17, further comprising renormalizing at least a portion of the encrypted result set.

19. The method of claim 1, wherein the homomorphic work space is built on top of one or more HE primitives selected from an HE library, and the at least one homomorphic operation is created from the one or more HE primitives.

20. A non-transitory computer readable storage medium on which are stored instructions executable by a processor to perform operations for providing access to an encrypted result set, the operations comprising:
    creating a homomorphic encryption (HE) context among at least two computing devices;
    instantiating, at least in part based on the HE context, a homomorphic work space (HWS) in a non-transitory, computer readable first memory of a first computing device of the at least two computing devices wherein the HWS is distributed among the at least two computing devices;
    loading encrypted data into the first memory, wherein the encrypted data is encrypted according to the HE context and wherein the first computing device lacks access to an unencrypted version of the encrypted data;
    generating an encrypted result set in the first memory by executing at least one homomorphic operation on at least a portion of the encrypted data according to instructions from a second computing device of the at least two computing devices;
    serializing at least the encrypted result set as a serialized object;

transmitting, over a network, the serialized object including at least the encrypted result set to the second computing device.

21. A system for providing access to an encrypted result set, the system comprising:
- a first computing device for creating a homomorphic encryption (HE) context among at least two computing devices including the first computing device, instantiating, at least in part based on the HE context, a homomorphic work space (HWS) in a non-transitory, computer readable first memory of the first computing device, and loading encrypted data into the first memory, wherein the HWS is distributed among the at least two computing devices, wherein the encrypted data is encrypted according to the HE context, and wherein the first computing device lacks access to an unencrypted version of the encrypted data; and
- a second computing device of the at least two computing devices for providing instructions to execute at least one homomorphic operation on at least a portion of the encrypted data,
- wherein the first computing device generates an encrypted result set in the first memory by executing the at least one homomorphic operation on the at least a portion of the encrypted data according to the instructions, serializes at least the encrypted result set as a serialized object, and transmits, over a network, the serialized object including at least the encrypted result set to the second computing device.

* * * * *